(12) United States Patent
He

(10) Patent No.: US 7,957,805 B2
(45) Date of Patent: Jun. 7, 2011

(54) IMPLANTABLE MICROSTIMULATOR WITH EXTERNAL ELECTRODES DISPOSED ON A FILM SUBSTRATE AND METHODS OF MANUFACTURE AND USE

(75) Inventor: Tom Xiaohai He, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 981 days.

(21) Appl. No.: 11/142,154

(22) Filed: Jun. 1, 2005

(65) Prior Publication Data
US 2006/0276842 A1  Dec. 7, 2006

(51) Int. Cl.
*A61N 1/00* (2006.01)
(52) U.S. Cl. ............ 607/36; 607/2; 607/37; 607/39; 607/40
(58) Field of Classification Search .......... 607/12, 607/36, 39–40, 37
See application file for complete search history.

(56) References Cited

U.S. PATENT DOCUMENTS

| | | | |
|---|---|---|---|
| 3,718,142 A | | 2/1973 | Mulier |
| 3,926,198 A | * | 12/1975 | Kolenik .......... 607/36 |
| 4,254,775 A | * | 3/1981 | Langer ............ 607/5 |
| 5,103,818 A | * | 4/1992 | Maston et al. ...... 607/9 |
| 5,193,539 A | | 3/1993 | Schulman et al. |
| 5,193,540 A | | 3/1993 | Schulman et al. |
| 5,207,218 A | * | 5/1993 | Carpentier et al. ... 607/36 |
| 5,312,439 A | | 5/1994 | Loeb |
| 5,314,458 A | * | 5/1994 | Najafi et al. ........ 607/116 |
| 5,535,097 A | * | 7/1996 | Ruben et al. ....... 361/736 |
| 5,607,463 A | * | 3/1997 | Schwartz et al. ..... 623/1.44 |
| 5,645,572 A | * | 7/1997 | Kroll et al. ........ 607/5 |
| 5,755,743 A | * | 5/1998 | Volz et al. ......... 607/37 |
| 5,817,130 A | * | 10/1998 | Cox et al. .......... 607/5 |
| 5,895,980 A | * | 4/1999 | Thompson .......... 607/36 |
| 6,051,017 A | * | 4/2000 | Loeb et al. ......... 607/1 |
| 6,315,721 B2 | * | 11/2001 | Schulman et al. ..... 600/301 |
| 6,453,199 B1 | * | 9/2002 | Kobozev ........... 607/40 |
| 6,609,032 B1 | | 8/2003 | Woods et al. |
| 7,047,074 B2 | * | 5/2006 | Connelly et al. ..... 607/36 |
| 2002/0171065 A1 | * | 11/2002 | Lochun et al. ...... 252/500 |
| 2003/0097166 A1 | * | 5/2003 | Krulevitch et al. .... 607/116 |

(Continued)

FOREIGN PATENT DOCUMENTS

EP  534782 A1 * 3/1993

(Continued)

OTHER PUBLICATIONS

U.S. Appl. No. 11/056,762, filed Feb. 11, 2005, Inventor He, "An Implantable Microstimulator Having a Separate Battery Unit and Methods of Use Thereof". U.S. Appl. No. 11/040,209, filed Jan. 20, 2005, Inventor Colvin et al., "Implantable Microstimulator with Plastic Housing and Methods of Manufacture and Use".

*Primary Examiner* — Niketa I Patel
*Assistant Examiner* — Nicole F Lavert
(74) *Attorney, Agent, or Firm* — Frommer Lawrence & Haug LLP; Bruce E. Black

(57) ABSTRACT

An implantable microstimulator includes a housing, an electronic subassembly, conductive vias, and an electrode arrangement. The housing defines an interior and an exterior with the electronic subassembly disposed in the interior of the housing. The conductive vias extend from the interior to the exterior of the housing. The electrode arrangement is disposed on the housing and includes a film substrate with electrodes disposed on the film substrate and coupled to the electronic subassembly through the plurality of vias.

20 Claims, 4 Drawing Sheets

U.S. PATENT DOCUMENTS

| | | | |
|---|---|---|---|
| 2004/0059392 A1* | 3/2004 | Parramon et al. | 607/36 |
| 2004/0068298 A1* | 4/2004 | Parramon et al. | 607/2 |
| 2004/0260372 A1* | 12/2004 | Canfield et al. | 607/116 |
| 2006/0212075 A1* | 9/2006 | Marnfeldt | 607/2 |

FOREIGN PATENT DOCUMENTS

| | | |
|---|---|---|
| WO | WO 98/37926 | 9/1998 |
| WO | WO 98/43700 | 10/1998 |
| WO | WO 98/43701 | 10/1998 |

* cited by examiner

US 7,957,805 B2

IMPLANTABLE MICROSTIMULATOR WITH EXTERNAL ELECTRODES DISPOSED ON A FILM SUBSTRATE AND METHODS OF MANUFACTURE AND USE

FIELD

The invention is directed to implantable microstimulators with one or more external electrodes and methods of manufacturing and using the devices. In addition, the invention is directed to implantable microstimulators with one or more external electrodes disposed on a film substrate and methods of manufacturing and using the devices.

BACKGROUND

Implantable microstimulators have been developed to provide therapy for a variety of disorders, as well as other treatments. For example, implantable microstimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Implantable microstimulators, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissue. It is preferable that the electronic circuitry and power source be held within the housing in a hermetically-sealed environment for the protection of the user and the protection of the circuitry and power source. Once implanted, it is often preferable that the microstimulator can be controlled and/or that the electrical source can be charged without removing the microstimulator from the implanted environment.

The electrodes used for a microstimulator with a cylindrical housing are often disposed at the ends of the housing or in rings around the housing. This provides 360° stimulation around the microstimulator. In at least some applications, however, the tissue to be stimulated is positioned on only one side of the microstimulator. Therefore, some of the energy produced by the microstimulator is not productively used in stimulating the desired tissue.

BRIEF SUMMARY

One embodiment is an implantable microstimulator that includes a housing, an electronic subassembly, conductive vias, and an electrode arrangement. The housing defines an interior and an exterior with the electronic subassembly disposed in the interior of the housing. The conductive vias extend from the interior to the exterior of the housing. The electrode arrangement is disposed on the housing and includes a film substrate with electrodes disposed on the film substrate and coupled to the electronic subassembly through the plurality of vias.

Another embodiment is an implantable device that includes a housing, an electronic subassembly, conductive vias, a film substrate, and a support member. The housing defines an interior and an exterior with the electronic subassembly disposed in the interior of the housing. Conductive vias extend from the interior to the exterior of the housing. The film substrate has contact pads in electrical contact with the conductive vias. The support member is coupled to the housing and disposed over the substrate and vias and applies pressure to the substrate to maintain the electrical contact between the vias and the contact pads.

Yet another embodiment is a method of making an implantable microstimulator. An electronic subassembly is placed into a non-conductive housing and conductive vias are formed through the housing. Electrodes, conductors, and contact pads are formed on a film substrate with the conductors coupling the electrodes to the contact pads. The film substrate is disposed on the housing with the contact pads in electrical communication with the vias. The electronic subassembly is coupled to the conductive vias.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to implantable microstimulators with one or more external electrodes and methods of manufacturing and using the devices. In addition, the invention is directed to implantable microstimulators with one or more external electrodes disposed on a film substrate and methods of manufacturing and using the devices.

Previously, implantable microstimulators have been made using housing and electrodes often disposed at the end(s) of the housing. Examples of such microstimulators are found in U.S. Pat. Nos. 5,139,539; 5,239,540; 5,312,439; 6,051,017; 6,609,032; U.S. Patent Application Publication No. 2004/0059392, now U.S. Pat. No. 7,437,193 issued Oct. 14, 2008 and PCT Patent Applications Publication Nos. 98/37926; 98/43700; and 98/43701.

An implantable microstimulator can include a housing with one or more electrodes on a film substrate that is disposed on the exterior surface of the housing. Conductive vias through the housing provide contact with contact pads disposed on the film substrate to couple the electrodes with an electronic subassembly disposed within the housing. A support structure can also be provided to apply pressure to the film substrate and maintain contact between the contact pads and conductive vias.

In at least some embodiments, electrodes on only one side of the implantable microstimulator can be selected to provide stimulation of the desired tissue. This may provide more efficient stimulation of the tissue when compared to an implantable microstimulator with electrodes disposed on more than one side of the microstimulator or electrodes which provide roughly 360° stimulation from a portion (e.g., the tip) of the microstimulator.

Figure 1:
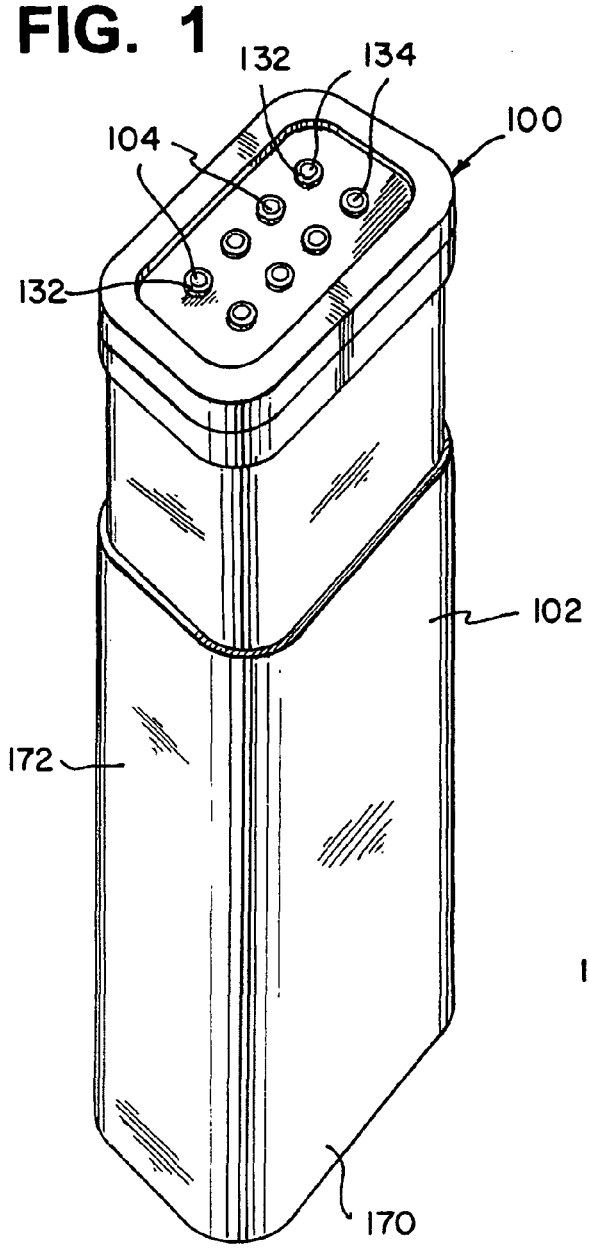
FIG. 1 is a perspective view of one embodiment of a portion of a microstimulator, according to the invention.
Figure 2:
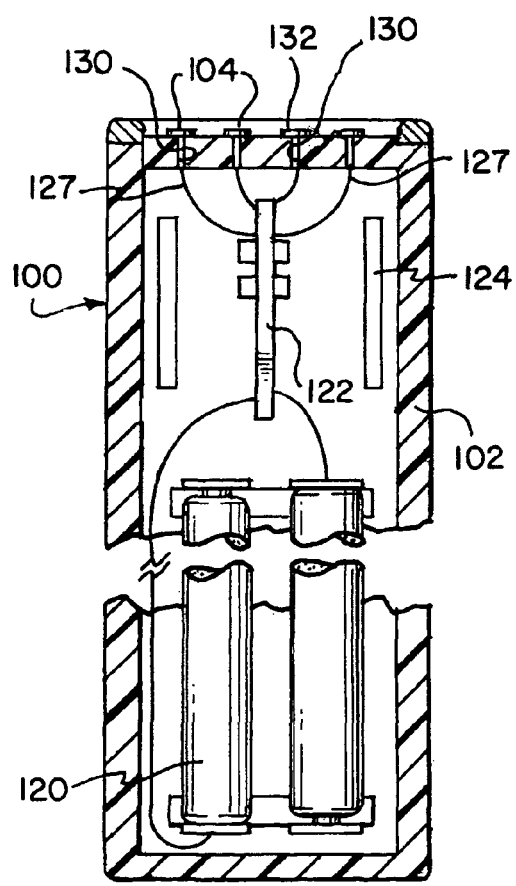
FIG. 2 is a cross-sectional view of one embodiment of a portion of a microstimulator, according to the invention.

FIGS. 1 and 2 illustrate a portion 100 of one embodiment of an implantable microstimulator. The implantable microstimulator includes a housing 102, a power source 120, an electronics subassembly 122, an optional antenna 124, one or more conductors 127 extending from the electronics subassembly 122 to the conductive via(s) 104, and one or more conductive vias 104 extending through the housing to couple the electronic subassembly to electrodes disposed on the exterior of the housing. Other embodiments of an implantable microstimulator may include more or fewer components. It will be understood that the power source 120, components of the electronics subassembly 122, and/or the optional antenna 124 can be provided outside of the housing in a separate unit and coupled to the implantable microstimulator by a lead. Examples of such arrangements are described in U.S. patent application Ser. No. 11/056,762, incorporated herein by reference.

Figure 3:
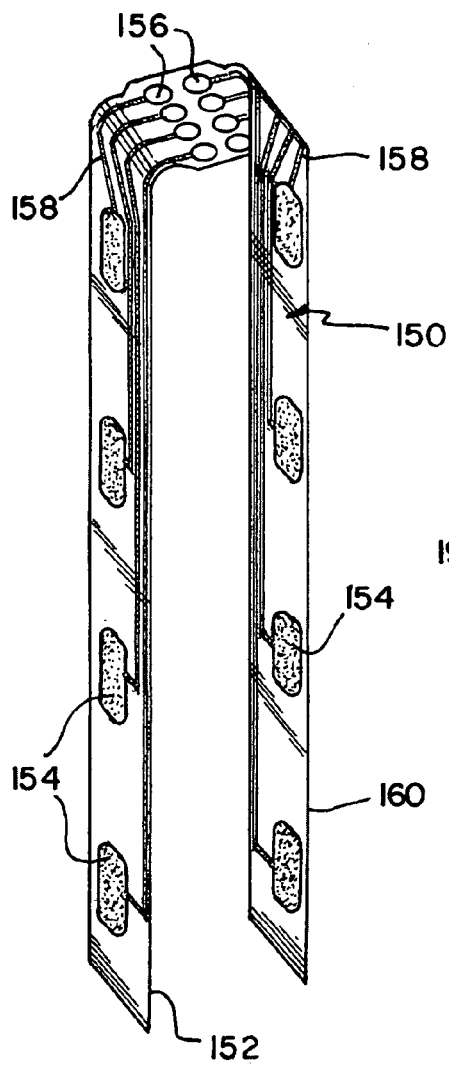
FIG. 3 is a perspective view of one embodiment of external electrodes disposed on a film substrate for use in a microstimulator, according to the invention.
Figure 4:
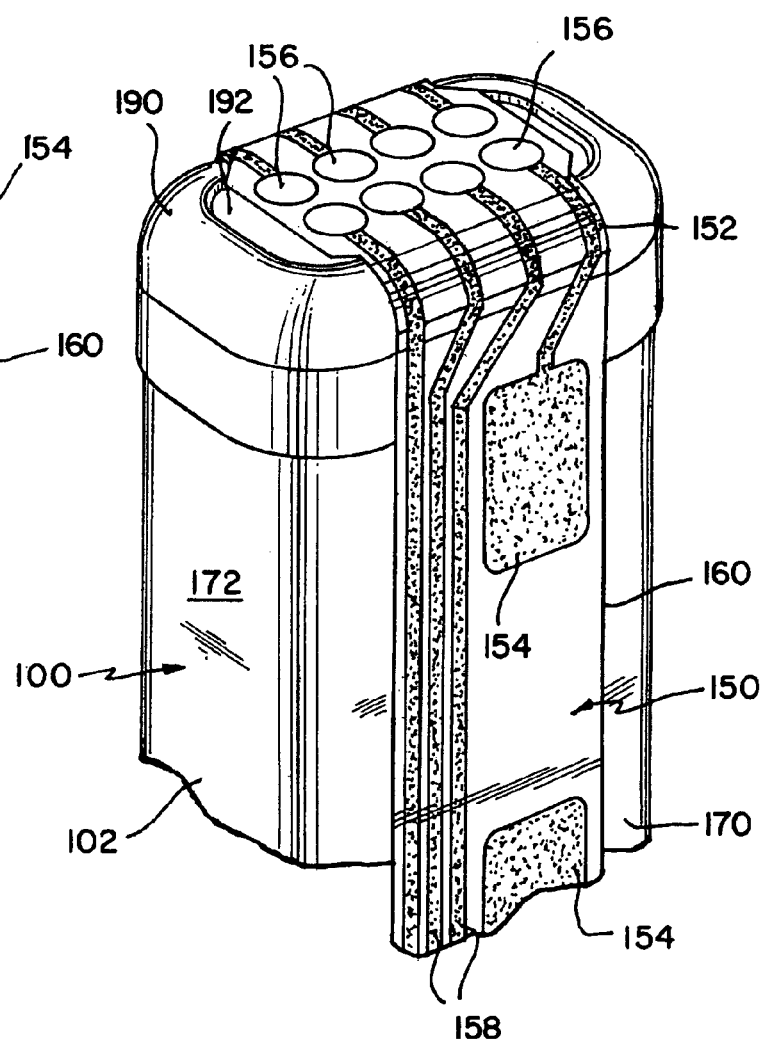
FIG. 4 is a perspective view of the portion of FIG. 2 and the electrodes/substrate of FIG. 3 disposed together to form a microstimulator, according to the invention.

FIG. 3 illustrates a second portion 150 of the implantable microstimulator. This portion includes a first substrate 152, one or more electrodes 154, one or more contact pads 156, conductor(s) 158 coupling the electrode(s) 154 to the contact pad(s) 156, and optionally a second substrate 160 disposed over the first substrate so that at least a portion of the conductors is disposed between the first and second substrates. FIG. 4 illustrates the two portions 100, 150 (FIGS. 2 and 3) coupled together with the contact pads 156 disposed over the vias 104 (FIG. 1) so that the electrode(s) 154 are coupled to the electronic subassembly 122 (FIG. 2) within the housing 102.

The housing 102 can be formed of any material that resists the transport of moisture into the interior of the housing and is sufficiently sturdy to protect the components on the interior of the housing from damage under expected implantation and usage conditions. At least the portion of the housing 102 adjacent to the vias 104 is non-conductive. In some embodiments, the housing is entirely non-conductive. Suitable materials for the housing (or a portion of the housing) include metals, ceramics, and plastics.

The housing can have any shape including, for example, cylindrical, parallelepiped, cubic, and the like. In at least some embodiments, a non-cylindrical shape (for example, a parallelepiped shape) is preferred. The non-cylindrical shape can aid a practitioner in positioning the microstimulator correctly in relation to the tissue to be stimulated. In some embodiments, the shape has sides which are distinguishable based on at least one dimension. In the illustrated embodiment of FIGS. 1-4, the housing 102 has a roughly parallelepiped shape with two opposing sides 170 that are wider than two adjacent sides 172. This difference in dimension can aid the practitioner implanting the device in correctly positioning the microstimulator relative to the tissue to be stimulated. For example, as illustrated in the embodiment of FIGS. 1-4, the electrodes 154 can be disposed on the wider side(s) 170 so that the practitioner can identify which side (for example, one of the wider sides) should be positioned adjacent the tissue to be stimulated. In one embodiment, electrodes are provided on both of the wider sides of the housing so that a practitioner does not need to identify which of the two sides has electrodes. This can facilitate quicker implantation of the device into the patient.

The lateral width of a side of the housing can be the same or can vary along the length of the housing. The width of a side can be, for example, no greater then 5 mm, no greater than 4 mm, no greater than 3.3 mm, or no greater than 3 mm. This width can be in the range of from, for example, 1 to 5 mm.

In at least some embodiments, the length of the microstimulator is no greater than 30 mm. Typically the length of the microstimulator is in the range of 10 to 30 mm.

Optionally, the housing can be covered, in full or in part, with a coating. The coating can be provided to improve or alter one or more properties of the housing including, for example, biocompatibility, hydrophobicity, moisture permeability, leaching of material into or out of the housing, and the like. The optional coating can be a polymer material, inorganic material, or organic material. As an example, the housing may be coated with an inorganic material, such as, for example, silicon dioxide, silicon nitride, titanium dioxide, or the like, to reduce moisture permeability. As another example, a silicone coating may be used to improve biocompatibility. In yet another example, a coating can be applied which contains a compound, such as, for example, a drug, prodrug, hormone, or other bioactive molecule, that can be released over time when the microstimulator is implanted. (In another embodiment, a plastic housing may include such a compound to be released over time after implantation.) In some embodiments, the coating includes two or more layers of the same or different materials.

The formation of the coating can be accomplished using any method including, for example, dip-coating, sputtering, reactive sputtering, physical or chemical vapor deposition, spray coating, and the like. The coating can be applied before the other microstimulator components have been assembled with the housing or at any other point in the microstimulator manufacturing process including applying the coating after the microstimulator has been completely assembled. Typically, the coating is non-conductive.

The one or more conductive vias 104 are provided through a non-conductive portion of the housing 102. In at least some embodiments, there are at least two conductive vias, but there can be any number of vias including two, four, six, eight, ten, or more conductive vias. The conductive vias 104 can all be formed through a single side of the housing 102, as illustrated in FIGS. 1 and 2 or vias can be formed through two or more sides of the housing. The vias 104 are typically filled with a conductive material such as a metal (including alloys). The vias 104 are used to couple the electrodes 154 to the electronic subassembly 122 which provides the stimulation signals to the electrodes.

In the illustrated embodiment, each via includes a channel 130 through the housing, a capture pad 132 disposed on the surface of the housing 102, and an optional protrusion 134 (FIG. 1) that can facilitate alignment and contact with the contact pads 156. Optionally, capture pads (not shown) can also be formed on the interior surface of the housing to facilitate connection of the conductors 127 to the vias 104. In one example of forming the vias, a non-conductive plate (e.g., a ceramic plate) is provided with holes through the plate. For example, the holes can be provided in the plate by molding them in the plate or drilling the plate. The holes are filled with metal or other conductive material to form the channels of the via. For example, a platinum (or other metal) paste can be disposed in holes of a green state ceramic plate and then the plate and paste can be fired. In some instances, firing the ceramic plate may alter the position of the vias slightly. Providing the wider capture pads 132 over the vias 104 can reduce tolerances for registration of the contact pads 156 with the vias to maintain good electrical contact.

In one example of forming the capture pads, a metal layer can be disposed on a surface of the plate and then the metal layer can be patterned using conventional techniques to form the capture pads 132 and optional protrusions 134. For example, a metal layer can be sputtered, or otherwise deposited using methods such as physical vapor deposition, chemical vapor deposition, electroplating, and electroless plating, onto the surface of the plate. The metal layer can be selectively etched to form the capture pads. Using capture pads that are larger in diameter than the vias can make connection with the contact pads easier and less sensitive to alignment.

Turning to FIG. 3 and portion 150 of the microstimulator, the first substrate 152 can be a thin film substrate. The first substrate can be made of any suitable non-conductive material including polymers/plastics. The selected material should be suitable for the formation of electrodes, contact pads, and conductors on the material and it should be biocompatible. One example of a suitable material is polyimide.

The contact pads 156, conductors, 158, and electrodes 154 can be disposed on the first substrate 152 in any manner. For example, a metal layer can be disposed on the first substrate 152 and the contact pads 156, conductors, 158, and electrodes 154 can be formed by etching the metal layer. Any deposition technique can be used to form the metal layer including physical vapor deposition, chemical vapor deposition, sputtering, and the like. Conventional etching techniques can be used to form the desired structures. In another example, the contact pads 156, conductors, 158, and electrodes 154 can be formed by printing these components onto the substrate 152 using a conductive ink.

A portion of the first substrate underneath the contact pads 156 can be removed (for example, by etching) to expose the contact pads 156 to allow them to make contact with the capture pads 132 on the housing 102. As one alternative, the contact pads can be formed on a side of the first substrate opposite the conductors and electrodes and vias can be formed through the first substrate and filled with conductive material to couple the contact pads to the conductors.

The first substrate 152 can have a variety of shapes and configurations. The substrate can be formed so that it can be disposed on two or more sides of the housing 102 or on a single side of the housing. In the illustrated example, the substrate is disposed on three sides of the housing. In some embodiments (such as the illustrated example), a substrate shape is selected so that electrodes can be disposed on two or more sides of the housing. In the illustrated example, electrodes are disposed on opposing sides of the housing. In other embodiments, electrodes may only be disposed on one side of the housing.

Preferably, the first substrate 152 is attached to the housing 102 so that the first substrate does not move relative to the housing. For example, the first substrate can be adhesively mounted onto the housing.

Optionally, a second substrate 160 is disposed over at least a portion of the contact pads 156 and/or conductors 158. The second substrate can be a single piece of material or can be several separate pieces. Preferably, the second substrate 160 leaves at least a portion of the electrodes 154 exposed. For example, the second substrate 160 can be selectively etched or die cut to expose the electrodes. The second substrate can be made of the same or a different material than the first substrate. The second substrate can be coupled to the first substrate using any method, including welding at least a portion of the first and second substrates together (e.g., around the periphery of the substrates) or adhesively mounting the second substrate on the first substrate. The second substrate 160 can provide protection for the conductors 158 and/or contact pads 156. In addition, the second substrate can provide support for the contact pads when a portion of the first substrate is removed to expose the contact pads to permit contact with the capture pads 132.

The electrodes 154 typically form the anode and cathode of the microstimulator. The electronic subassembly may be configured to allow each individual electrode to selectably operate as an anode or cathode or some electrodes may be designated as operable as cathodes only and other electrodes designated as operable as anodes only. In addition, the electronic subassembly may be configured to allow multiple anodes and/or cathodes or may be configured to allow only one electrode to be an anode and one electrode to be a cathode at any given time.

The electrodes 154, conductors 158, and contact pads 156 can be formed using any conductive material. Examples of suitable materials include metals, alloys, conductive polymers/plastics, and conductive carbon.

Figure 5:
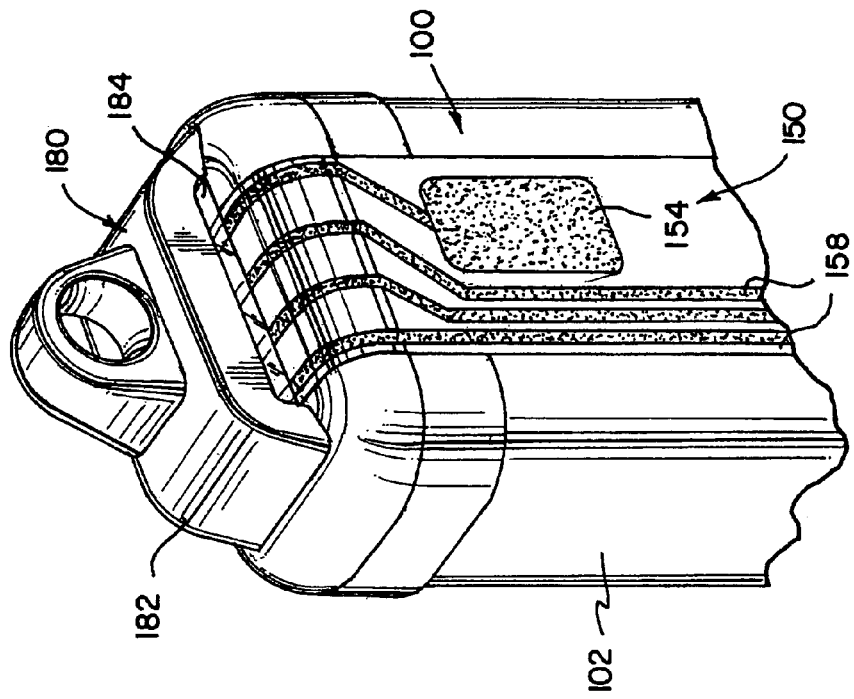
FIG. 5 is a perspective side view of one embodiment of a microstimulator with a support element, according to the invention.
Figure 6:
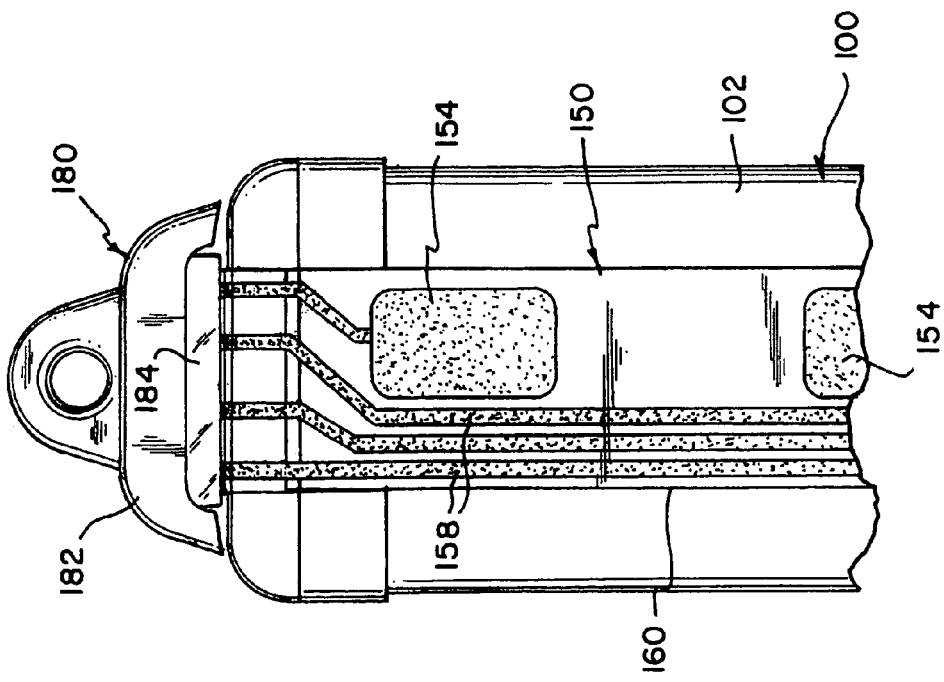
FIG. 6 is a perspective view from a different angle of the microstimulator of FIG. 5.

In some embodiments, the microstimulator includes a support member 180, as illustrated in FIGS. 5 and 6, to facilitate and maintain contact between the contact pads 156 on the first substrate 152 and the capture pads 132/vias 104 on the housing 102. The support member applies pressure to maintain the contact.

In one embodiment, the support member 180 includes a bridge 182 and a contact element 184. The bridge 182 is provided to attach the support member 180 to the housing 102 and hold the contact element 184 in place. As one example, a bridge can be made of metal and can be welded to a metallic portion of the housing. For example (as best illustrated in FIG. 4), a metallic ring 190 can be brazed to a ceramic portion 192 of the housing 102 which contains the vias 104. The metallic bridge 182 is welded or otherwise attached to the metallic ring 190.

The contact element 184 is disposed between the bridge 182 and the housing 102. Preferably, the contact element 184 is formed of a non-conductive material. Preferably, the material of the contact element 184 is resilient and somewhat compressible. Such an arrangement may permit easier assembly as the resilient material can be slightly deformed to allow conformation of the contact element with the contact pads/capture pads. One example of such a material is silicone rubber, such as SILASTIC™.

Returning to FIG. 2, a power source 120 can be disposed within the housing 100. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, now U.S. Pat. No. 7,437,193, incorporated herein by reference.

As another alternative, power can be supplied by an external power source through inductive coupling via the optional antenna 124 or a secondary antenna. The external power source can be in a device that is mounted on the skin of the user or in a unit that is provided near the microstimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 7) external to the user. Examples of such arrangements can be found in the microstimulator references identified above.

Figure 7:
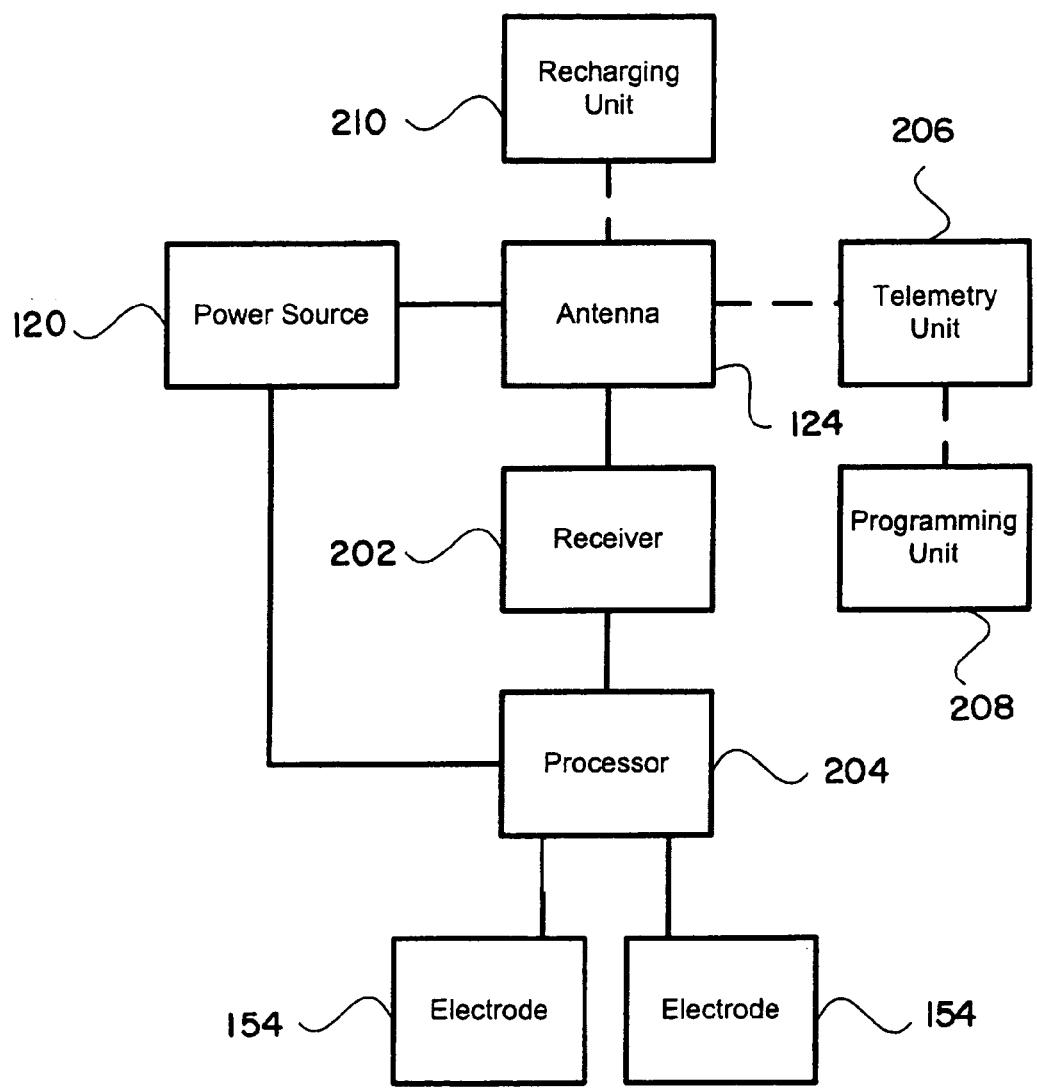
FIG. 7 is a schematic overview of components for a system for microstimulation of body tissues, according to the invention.

In one embodiment, electrical current is emitted by the electrodes 154 to stimulate motor nerve fibers, muscle fibers, or other body tissues near the microstimulator. The electronic subassembly 122 provides the electronics used to operate the microstimulator and generate the electrical pulses at the electrodes 154 to produce stimulation of the body tissues. FIG. 7 illustrates one embodiment of components of the electronic subassembly and associated units. It will be understood that the electronic subassembly can include more, fewer, or different components and can have a variety of different configurations including those configurations disclosed in the microstimulator references cited above. Some or all of the components of the electronic subassembly can be positioned on one or more circuit boards or similar carriers within the housing, if desired.

In the illustrated embodiment, a processor 204 is provided to control the timing and electrical characteristics of the microstimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments with electrodes disposed on two or more sides of the housing, the processor may be used to identify which electrodes provide the most useful stimulation of the desired tissue. This process may be performed using an external programming unit, as described below, that is in communication with the processor 204.

Any processor can be used and can be as simple as an electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics and the selection of electrodes, if desired.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the implanted microstimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the microstimulator. For example, the signals may be used to modify the pulses of the microstimulator such as modifying one or more of pulse duration, pulse frequency, pulse waveform, and pulse strength. The signals may also direct the microstimulator to cease operation or to start operation or to start charging the battery.

Optionally, the microstimulator may include a transmitter (not shown) coupled to the processor and antenna for transmitting signals back to the telemetry unit 206 or another unit capable of receiving the signals. For example, the microstimulator may transmit signals indicating whether the microstimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within or on the housing.

Any method of manufacture of the microstimulator can be used. For example, the electronic subassembly, power source, and antenna can be manufactured as described in U.S. Patent Application No. 2004/0059392, now U.S. Pat. No. 7,437,193. These components can then be placed inside the housing (or, alternatively, the housing can be formed, e.g., molded, around the components). The portion 150 of the microstimulator containing the film substrate 152 and electrodes 154, as well as the vias 104 in the housing 102, can be formed as described above. Coatings on the electrodes or housing, if any, can be applied at appropriate points during the manufacturing process.

The microstimulator can be implanted into the body tissue using a variety of methods including surgical methods. In some embodiments, the microstimulator can be implanted using a hypodermic needle or other insertion cannula. Examples of insertion techniques can be found in U.S. Pat. No. 6,051,017.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable microstimulator, comprising:
   a housing defining an interior and an exterior;
   an electronic subassembly disposed in the interior of, and surrounded by, the housing;
   a plurality of conductive vias electrically coupled to the subassembly and extending from the interior to the exterior of the housing;
   an electrode arrangement disposed on the housing and comprising
      a flexible, non-conductive, polymer film substrate external to the housing and disposed over a portion of the exterior of the housing and forming a portion of an exterior surface of the microstimulator, and
      a plurality of thin electrodes disposed entirely on the film substrate and exposed on an exterior of the implantable microstimulator, wherein the plurality of electrodes are separated from the housing by the film substrate and the plurality of electrodes are coupled to the electronic subassembly through the plurality of conductive vias and are configured and arranged to stimulate adjacent tissue when implanted; and
   a plurality of conductors disposed on the film substrate and electrically coupling the plurality of electrodes to the plurality of conductive vias.

2. The implantable microstimulator of claim 1, wherein the electrode arrangement further comprises a plurality of contact pads disposed on the film substrate, wherein the contact pads are configured and arranged to make contact with the conductive vias at the exterior of the housing.

3. The implantable microstimulator of claim 1, wherein the electrode arrangement further comprises a second film substrate disposed over at least a portion of the conductors, wherein the portion of the conductors is disposed between the first film substrate and the second film substrate.

4. The implantable microstimulator of claim 2, wherein the contact pads are exposed through the film substrate.

5. The implantable microstimulator of claim 1, wherein the vias comprise a capture pad disposed over a conductive channel through the housing.

6. The implantable microstimulator of claim 1, wherein the housing is non-cylindrical.

7. The implantable microstimulator of claim 6, wherein the film substrate is disposed over a portion of at least two opposing sides of the housing.

8. The implantable microstimulator of claim 7, wherein the plurality of electrodes are disposed over each of the at least two opposing sides of the housing.

9. The implantable microstimulator of claim 2, further comprising a support member coupled to the housing and disposed over the film substrate and vias and applying pressure to the substrate to maintain the electrical contact between the vias and the contact pads on the film substrate.

10. An implantable device, comprising:
    a housing defining an interior and an exterior;
    an electronic subassembly disposed in the interior of, and surrounded by, the housing;
    a plurality of conductive vias electrically coupled to the subassembly and extending from the interior to the exterior of the housing;
    a flexible, polymer film substrate external to the housing and forming a portion of the exterior of the implantable device and having a plurality of electrodes and a plurality of contact pads entirely disposed thereon, wherein the plurality of contact pads are in electrical contact with the plurality of conductive vias and the plurality of electrodes and wherein the plurality of electrodes are separated from the housing by the film substrate;
    a plurality of conductors disposed on the film substrate and electrically coupling the plurality of electrodes to the plurality of conductive vias; and
    a support member coupled to the housing and disposed over the substrate and the vias, the support member applying pressure to the substrate to maintain the electrical contact between the vias and the contact pads,
    wherein the plurality of electrodes are exposed on an exterior of the implantable microstimulator and are configured and arranged to stimulate adjacent tissue when implanted.

11. The implantable device of claim 10, wherein the support member comprises a bridge that extends from portions of the housing on opposite sides of the film substrate and a pressure member disposed between the bridge and the substrate.

12. The implantable device of claim 11, wherein the pressure member comprises a compressible material.

13. The implantable device of claim 11, wherein the bridge is metal and the housing comprises an annular metal endcap to which the bridge is welded.

14. The implantable device of claim 10, wherein the housing comprises a ceramic piece through which the vias are disposed.

15. The implantable device of claim 10, wherein the housing comprises a first end and the vias are disposed at the first end of the housing.

16. A method of making an implantable microstimulator, the method comprising:
    placing an electronic subassembly into, and surrounded by, a non-conductive housing;
    forming a plurality of conductive vias through the housing;
    forming a plurality of electrodes, conductors, and contact pads on a flexible, polymer film substrate, the conductors coupling the electrodes to the contact pads, wherein the plurality of electrodes are separated from the housing by the film substrate;
    disposing the film substrate, which is external to the housing, over a portion of an exterior of the housing with the contact pads in electrical communication with the conductive vias, wherein the film substrate forms a portion of an exterior surface of the implantable microstimulator; and
    coupling the electronic subassembly to the conductive vias,
    wherein the plurality of electrodes are exposed on an exterior of the implantable microstimulator and are configured and arranged to stimulate adjacent tissue when implanted.

17. The method of claim 16, further comprising disposing a support member over the substrate and vias and applying pressure to the substrate to maintain the electrical contact between the vias and contact pads.

18. The method of claim 17, further comprising coupling the support member to the housing.

19. The method of claim 16, further comprising placing a second film substrate over the film substrate and at least a portion of the conductors, wherein the portion of the conductors is between the film substrate and the second film substrate.

20. The method of claim 16, wherein disposing the film substrate on the housing comprises disposing the film substrate over a portion the housing with electrodes disposed over opposing sides of the housing.

* * * * *